United States Patent
Limburg et al.

(10) Patent No.: US 12,301,782 B2
(45) Date of Patent: May 13, 2025

(54) METHODS AND DEVICES FOR PERFORMING AN ANALYTICAL MEASUREMENT

(71) Applicant: Roche Diabetes Care, Inc., Indianapolis, IN (US)

(72) Inventors: Bernhard Limburg, Soergenloch (DE); Herbert Wieder, Lampertheim (DE); Max Berg, Mannheim (DE); Simon Wetzel, Mannheim (DE); Daniel Sieffert, Mannheim (DE); Fredrik Hailer, Mannheim (DE); Christian Melchinger, Mannheim (DE); Zied Guermazi, Weinheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 673 days.

(21) Appl. No.: 17/308,665

(22) Filed: May 5, 2021

(65) Prior Publication Data
US 2021/0258565 A1    Aug. 19, 2021

Related U.S. Application Data

(63) Continuation of application No. PCT/EP2019/079332, filed on Oct. 28, 2019.

(30) Foreign Application Priority Data

Nov. 7, 2018  (EP) ..................... 18205003

(51) Int. Cl.
H04N 17/00    (2006.01)
A61B 5/1495   (2006.01)
(Continued)

(52) U.S. Cl.
CPC ......... *H04N 17/002* (2013.01); *A61B 5/1495* (2013.01); *G01N 21/78* (2013.01);
(Continued)

(58) Field of Classification Search
None
See application file for complete search history.

(56) References Cited

U.S. PATENT DOCUMENTS 9,550,021 B2    1/2017  Beden et al.
2008/0088858 A1  4/2008  Marcu et al.
(Continued)

FOREIGN PATENT DOCUMENTS

CN    101217674 A    7/2008
CN    102420995 A    4/2012
(Continued)

OTHER PUBLICATIONS

Unknown, Permissions overview, Android Developers, Oct. 12, 2018, XP055586158, Retrieved from the Internet: URL:https://web.archive.org/web/20181012010538/https://developer.android.com/guide/topics/permissions/overview, 20 pages.
(Continued)

*Primary Examiner* — Leon Flores
(74) *Attorney, Agent, or Firm* — Bose McKinney & Evans LLP (57) ABSTRACT

A method of evaluating the suitability of a mobile device for performing an analytical measurement based on a color formation reaction. The capability of the mobile device to have relevant settings of the mobile device controlled by software running on the mobile device is evaluated. The relevant settings pertain to image raw data processing steps to be carried out by the mobile device and may include a color space transformation and a tone mapping transformation. When the evaluation indicates that the mobile device is
(Continued)

capable of having the relevant settings controlled by the software, control information indicating that the mobile device is suitable for performing the analytical measurement is provided. When the evaluation indicates that the mobile device is not capable of having the relevant settings controlled by the software, control information indicating that the mobile device is unsuitable for performing the analytical measurement is provided.

14 Claims, 5 Drawing Sheets

(51) Int. Cl.
    *G01N 21/78* (2006.01)
    *G06T 7/80* (2017.01)
    *H04N 23/62* (2023.01)
    *A61B 5/145* (2006.01)
    *G01N 21/84* (2006.01)
    *G16H 10/40* (2018.01)

(52) U.S. Cl.
    CPC .............. *G06T 7/80* (2017.01); *H04N 23/62* (2023.01); *A61B 5/14532* (2013.01); *G01N 2021/8488* (2013.01); *G06T 2207/10024* (2013.01); *G16H 10/40* (2018.01)

(56) References Cited

U.S. PATENT DOCUMENTS

| | | |
|---|---|---|
| 2008/0165292 A1 | 7/2008 | Bing et al. |
| 2012/0181331 A1 | 7/2012 | Beden et al. |
| 2014/0072189 A1 | 3/2014 | Jena et al. |
| 2014/0154789 A1 | 6/2014 | Polwart et al. |
| 2015/0019157 A1 | 1/2015 | Denner et al. |
| 2016/0011178 A1 | 1/2016 | Hoenes et al. |
| 2016/0048739 A1 | 2/2016 | Burg |
| 2016/0080548 A1 | 3/2016 | Erickson et al. |
| 2020/0394775 A1* | 12/2020 | Andrivon ................. H04N 9/68 |
| 2021/0358172 A1 | 11/2021 | Bock et al. |

FOREIGN PATENT DOCUMENTS

| | | |
|---|---|---|
| CN | 104281733 A | 1/2015 |
| CN | 105393252 A | 3/2016 |
| JP | 2014-512196 A | 5/2014 |
| JP | 2015-533211 A | 11/2015 |
| KR | 10-2015-0119364 A | 10/2015 |
| RU | 2 582 268 C2 | 4/2016 |
| WO | WO 02/13136 A2 | 2/2002 |
| WO | WO 2014/037820 A2 | 3/2014 |
| WO | WO 2014/147074 A1 | 9/2014 |
| WO | WO 2014/172671 A1 | 10/2014 |
| WO | WO 2016/025935 A2 | 2/2016 |
| WO | WO 2018/149874 A1 | 8/2018 |

OTHER PUBLICATIONS

Uknown, Color space, Wikipedia, Aug. 25, 2018, XP055586406, Retrieved from the Internet: URL:https://en.wikipedia.org/w/index.php?title=Color_space&oldid=856541989, 6 pages.
Unknown, Tone mapping, Wikipedia, Oct. 30, 2018, XP055586398, Retrieved from the Internet: URL:https://en.wikipedia.org/w/index.php?title=Tone_mapping&oldid=866402779, 6 pages.
Hönes et al., Diabetes Technology and Therapeutics, vol. 10, Supplement 1, 2008, pp. 10-26.
International Search Report and Written Opinion of the International Searching Authority, PCT/EP2019/079332, Jan. 31, 2020, 11 pages.

* cited by examiner

METHODS AND DEVICES FOR PERFORMING AN ANALYTICAL MEASUREMENT

RELATED APPLICATIONS

This application is a continuation of PCT/EP2019/079332, filed on Oct. 28, 2019, which claims priority to EP 18 205 003.9, filed on Nov. 7, 2018, the entire disclosures of both of which are hereby incorporated herein by reference.

BACKGROUND

The present application refers to a method of evaluating the suitability of a mobile device for performing an analytical measurement, a method of calibrating a mobile device for performing an analytical measurement and a method of performing an analytical measurement. This disclosure further relates to a suitability computer program, a calibration computer program and a measurement computer program with programs for executing the methods according to this disclosure respectively. Further, this disclosure refers to a mobile device and a kit for performing one or more of the methods according to this disclosure. Methods, computer programs, mobile devices and kits according to this disclosure may be used in medical diagnostics, in order to for example qualitatively or quantitatively detect one or more analytes in one or more body fluids. Other fields of application of this disclosure, however, are possible.

In the field of medical diagnostics, in many cases, one or more analytes have to be detected in samples of a body fluid, such as blood, interstitial fluid, urine, saliva or other types of body fluids. Examples of analytes to be detected are glucose, triglycerides, lactate, cholesterol or other types of analytes typically present in these body fluids. According to the concentration and/or the presence of the analyte, an appropriate treatment may be chosen, if necessary. Without narrowing the scope, this disclosure specifically will be described with respect to blood glucose measurements. It shall be noted, however, that this disclosure may also be used for other types of analytical measurements using test elements.

Generally, devices and methods known to the skilled person make use of test elements comprising one or more test chemistries, which, in presence of the analyte to be detected, are capable of performing one or more detectable detection reactions, such as optically detectable detection reactions. With regard to these test chemistries, reference may be made, e.g., to J. Hoenes et al.: The Technology Behind Glucose Meters: Test Strips, Diabetes Technology & Therapeutics, Volume 10, Supplement 1, 2008, S-10 to S-26. Other types of test chemistry are possible and may be used for performing this disclosure.

Typically, one or more optically detectable changes in the test chemistry are monitored, in order to derive the concentration of the at least one analyte to be detected from these changes. For detecting the at least one change of optical properties of the test field, various types of detectors are known in the art. Thus, various types of light sources for illuminating the test fields as well as various types of detectors are known. In general, variable lighting conditions need to be taken into account. Thus, as an example WO 2016/25935 A2 discloses a diagnostic system for biological samples. The diagnostic system includes a diagnostic instrument, and a portable electronic device. The diagnostic instrument has a reference color bar and a plurality of chemical test pads to receive a biological sample. The portable electronic device includes a digital camera to capture a digital image of the diagnostic instrument in uncontrolled lightning environments, a sensor to capture illuminance of a surface of the diagnostic instrument, a processor coupled to the digital camera and sensor to receive the digital image and the illuminance, and a storage device coupled to the processor. The storage device stores instructions for execution by the processor to process the digital image and the illuminance, to normalize colors of the plurality of chemical test pads and determine diagnostic test results in response to quantification of color changes in the chemical test pads.

Besides using customized detectors which are specifically developed for the purpose of optically detecting changes in the test chemistry comprised by corresponding test elements, recent developments aim at using widely available devices such as smartphones. However, when using consumer-electronics having a camera, such as smartphones, may individual technical and optical properties need to be taken into account, since there is a vast number of cameras available on the market, which may have an impact on the determination of the analyte concentration.

U.S. Publication No. 2014/072189 A1 describes a system and method for analysis of colorimetric test strip strips and disease management. The system can include an accessory that is operably coupled to a mobile device, the mobile device acquiring and/or analyzing images of the colorimetric test strips. The light box accessory can be detachably attached to the mobile device, or made to remain attached to the mobile device, but with the capability of having the light box accessory removed from the field of view of the camera for general photography purposes.

The online article "Permissions Overview," Android Developers, 12 Oct. 2018 (2018-10-12), XP055586158, gives an overview on how Android permissions work, including: how permissions are presented to the user, the difference between install-time and runtime permission requests, how permissions are enforced, and the types of permissions and their groups.

U.S. Publication No. 2016/080548 A1 describes a method for obtaining a point-of-collection, selected quantitative indicia of an analyte on a test strip using a smartphone involving imaging a test strip on which a colorimetric reaction of a target sample has occurred due to test strip illumination by the smartphone. The smartphone includes a smartphone app and a smartphone accessory that provides an external environment-independent/internal light-free, imaging environment independent of the smartphone platform being used.

Thus, despite the advantages involved in using consumer-electronics having a camera for the purpose of detecting an analyte in a sample or evaluating analytical measurements, several technical challenges remain. In general, color representation in camera systems is adapted to provide images which are optimized in terms of human color perception, e.g., by internal post-processing of the raw data captured by the camera. However, such post-processing due to human color perception may not be ideal when aiming at accurately determining analyte concentrations in the sample.

SUMMARY

It is therefore desirable to provide methods and devices which address the above mentioned technical challenges of analytical measurements using mobile devices such as consumer-electronics mobile devices, specifically multipurpose mobile devices which are not dedicated to analytical measurements such as smartphones or tablet computers. Specifically, methods, computer programs and devices are disclosed which are widely applicable to available mobile devices and which are suited to increase measurement accuracy and improve reliability while allowing convenient handling for the user.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "camera," "image," "object," and "sample," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect, a method of evaluating the suitability of a mobile device for performing an analytical measurement based on a color formation reaction is disclosed. The mobile device has at least one camera. The method comprises the following steps which, as an example, may be performed in the given order. It shall be noted, however, that a different order is also possible. Further, it is also possible to perform one or more of the method steps once or repeatedly. Further, it is possible to perform two or more of the method steps simultaneously or in a timely overlapping fashion. The method may comprise further method steps which are not listed. In particular, the method of evaluating the suitability of a mobile device for performing an analytical measurement based on a color formation reaction may also be referred to as suitability method.

Generally, the method of evaluating the suitability of a mobile device for performing an analytical measurement based on a color formation reaction comprises the following steps:
  a) evaluating the capability of the mobile device and/or the camera to have one or more relevant settings of the mobile device and/or camera controlled by a user's software running on the mobile device, the relevant settings pertaining to image raw data processing steps to be carried out by the mobile device and/or camera, wherein the relevant settings include at least one of: a color space transformation and a tone mapping transformation, specifically by using a tone mapping curve;
  b) if the evaluation in step a) indicates that the mobile device and/or camera is capable of having the one or more relevant settings controlled by the user's software, providing at least one item of control information, specifically to one or more of the mobile device, the user or the user's software running on the mobile device, the at least one item of control information indicating that the mobile device, specifically the mobile device having the at least one camera, is suitable for performing the analytical measurement; and
  c) if the evaluation in step a) indicates that the mobile device and/or camera is not capable of having the one or more relevant settings controlled by the user's software, providing at least one item of control information, specifically to one or more of the mobile device, the user or the user's software running on the mobile device, the at least one item of control information indicating that the mobile device, specifically the mobile device having the at least one camera, is unsuitable for performing the analytical measurement.

The term "analytical measurement" as used herein is a broad term and is to be given its ordinary and customary meaning to a person of ordinary skill in the art and is not to be limited to a special or customized meaning. The term specifically may refer, without limitation, to a quantitatively and/or qualitatively determination of at least one analyte in an arbitrary sample. For example, the sample may comprise a body fluid, such as blood, interstitial fluid, urine, saliva or other types of body fluids. The result of the analytical measurement, as an example, may be a concentration of the analyte and/or the presence or absence of the analyte to be determined. Specifically, as an example, the analytical measurement may be a blood glucose measurement, thus the result of the analytical measurement may for example be a blood glucose concentration.

The at least one analyte, as an example, may be or may comprise one or more specific chemical compounds and/or other parameters. As an example, one or more analytes may be determined which take part in metabolism, such as blood glucose. Additionally or alternatively, other types of analytes or parameters may be determined, e.g., a pH value. The at least one sample, specifically, may be or may comprise at least one bodily fluid, such as blood, interstitial fluid, urine, saliva or the like. Additionally or alternatively, however, other types of samples may be used, such as water.

The term "mobile device" as used herein is a broad term and is to be given its ordinary and customary meaning to a person of ordinary skill in the art and is not to be limited to a special or customized meaning. The term specifically may refer, without limitation, to a mobile electronics device, more specifically to a mobile communication device such as a cell phone or smartphone. Additionally or alternatively, as will be outlined in further detail below, the mobile device may also refer to a tablet computer or another type of portable computer having at least one camera.

The term "camera" as used herein is a broad term and is to be given its ordinary and customary meaning to a person of ordinary skill in the art and is not to be limited to a special or customized meaning. The term specifically may refer, without limitation, to a device having at least one imaging element configured for recording or capturing spatially resolved one-dimensional, two-dimensional or even three-dimensional optical data or information. As an example, the camera may comprise at least one camera chip, such as at least one CCD chip and/or at least one CMOS chip configured for recording images. As used herein, without limitation, the term "image" specifically may relate to data recorded by using a camera, such as a plurality of electronic readings from the imaging device, such as the pixels of the camera chip.

The camera, besides the at least one camera chip or imaging chip, may comprise further elements, such as one or more optical elements, e.g., one or more lenses. As an example, the camera may be a fix-focus camera, having at least one lens which is fixedly adjusted with respect to the camera. Alternatively, however, the camera may also comprise one or more variable lenses which may be adjusted, automatically or manually. This disclosure specifically shall be applicable to cameras as usually used in mobile applications such as notebook computers, tablets or, specifically, cell phones such as smartphones. Thus, specifically, the camera may be part of a mobile device which, besides the at least one camera, comprises one or more data processing devices such as one or more data processors. Other cameras, however, are feasible.

The camera specifically may be a color camera. Thus, such as for each pixel, color information may be provided or generated, such as color values for three colors R, G, B. a larger number of color values is also feasible, such as four color values for each pixel, for example R, G, G, B. Color cameras are generally known to the skilled person. Thus, as an example, the camera chip may consist of a plurality of three or more different color sensors each, such as color recording pixels like one pixel for red (R), one pixel for green (G) and one pixel for blue (B). For each of the pixels, such as for R, G, B, values may be recorded by the pixels, such as digital values in the range of 0 to 255, depending on the intensity of the respective color. Instead of using color triples such as R, G, B, as an example, quadruples may be used, such as R, G, G, B. The color sensitivities of the pixels may be generated by color filters or by appropriate intrinsic sensitivities of the sensor elements used in the camera pixels. These techniques are generally known to the skilled person.

The term "relevant setting" as used herein is a broad term and is to be given its ordinary and customary meaning to a person of ordinary skill in the art and is not to be limited to a special or customized meaning. The term specifically may refer, without limitation, to an arbitrary configuration or adjustment considered to be pertinent for a specific function or operation. Specifically, the one or more relevant settings of the mobile device and/or the camera may specifically be or may comprise configurations considered to be pertinent for performing an analytical measurement based on a color formation reaction. Thus, as an example, the relevant settings of the mobile device and/or camera may refer to image processing configurations. In detail, the relevant settings pertain to image raw data processing steps. Specifically, the relevant settings include at least one of a color space transformation and a tone mapping correction. As stated above, the relevant settings of the mobile device may specifically be controlled by the user's software running on the mobile device. In particular, as used herein, the user's software may, for example, be or may comprise a software or program, such as a software app, for example an app downloaded from an app store or the like, running on the mobile device.

The term "color space transformation" as used herein is a broad term and is to be given its ordinary and customary meaning to a person of ordinary skill in the art and is not to be limited to a special or customized meaning. The term specifically may refer, without limitation, to an algorithm or operation of changing information from one first color space, e.g., from one specific mathematical representation of colors, into another color space, e.g., into a second color space, such as into another specific mathematical representation of colors. An arbitrary color may, for example, be represented in a first color space by a first mathematically structured information or data, such as by a first vector. Specifically, color space transformation may refer to changing representation of the color in the first color space into representation of the same color in the second color space. Thus, in particular, color space transformation may refer to changing the mathematically structured data, e.g., the vector, representing the color in the first color space, into the mathematically structured data or vector representing the color in the second color space. The color space transformation specifically may be or may comprise a matrix transformation, as will be explained in further exemplary detail below. Still, other transformations are feasible additionally or alternatively, such as a functional transformation.

As a simple example, color space transformation may be described by changing RBG input variables $R_{in}$, $B_{in}$ and $G_{in}$, into RGB output variables $R_{out}$, $B_{out}$ and $G_{out}$. Specifically, the color space transformation of the input variables into the output variables may be formed by matrix multiplication with a transformation matrix. In particular, in case that all non-diagonal elements of the transformation matrix equal zero, the RGB variables, e.g., RGB input and output variables, remain color-pure, specifically RGB values may not be mixed but only individually scaled.

Specifically, a relation between RGB input variables $R_{in}$, $B_{in}$ and $G_{in}$, and RGB output variables $R_{out}$, $B_{out}$ and $G_{out}$ may be described by the following equation:

$$\begin{pmatrix} R_{out} \\ G_{out} \\ B_{out} \end{pmatrix} = \begin{pmatrix} RR, RG, RB \\ GR, GG, GB \\ BR, BG, BB \end{pmatrix} * \begin{pmatrix} R_{in} \\ G_{in} \\ B_{in} \end{pmatrix} \quad (1)$$

Thus, in case all non-diagonal elements of the transformation matrix equal 0, the RGB output variables may be calculated by the following equations:

$$R_{out} = RR * R_{in} \quad (2.1)$$

$$G_{out} = GG * G_{in} \quad (2.2)$$

$$B_{out} = BB * B_{in} \quad (2.3)$$

However, in case non-diagonal elements of the transformation matrix do not equal zero, e.g., RG, RB, GR, GB, BR and BG≠0, the RGB output variables may be calculated by the following equations:

$$R_{out}=RR*R_{in}+RG*G_{in}*RB*B_{in} \quad (3.1)$$

$$G_{out}=GR*R_{in}+GG*G_{in}+GB*B_{in} \quad (3.2)$$

$$B_{out}=BR*R_{in}+BG*G_{in}+BB*B_{in} \quad (3.3)$$

The term "tone mapping transformation" as used herein is a broad term and is to be given its ordinary and customary meaning to a person of ordinary skill in the art and is not to be limited to a special or customized meaning. The term specifically may refer, without limitation, to a nonlinear compression of brightness dynamics. In particular, the tone mapping transformation may be or may comprise an algorithm or nonlinear operation of converting pixel-related brightness values of an image acquisition sensor or of the at least one camera chip, such as of at least one CCD chip and/or at least one CMOS chip configured for recording images, into brightness values in the image. Specifically, the tone mapping transformation may use a tone mapping curve establishing a relationship between a pixel brightness, wherein the pixel brightness may for example be measured in a linear scale, and a brightness value stored in the image for that pixel. Specifically, the tone mapping transformation may be carried out in form of transfer functions for a specific color space or for specific color channels. As an example, the tone mapping curve for a standard Red Green Blue color space (sRGB color space) comprises a Gamma correction.

The term "suitability" as used herein is a broad term and is to be given its ordinary and customary meaning to a person of ordinary skill in the art and is not to be limited to a special or customized meaning. The term specifically may refer, without limitation, to a property of an element or device for performing one or more predetermined functions. Thus, as an example, the suitability may be qualified or quantified by using one or more characteristics of the device. These one or more characteristics, as outlined above or as will be outlined in further detail below, may, individually or according to a predetermined combination, be evaluated by using one or more conditions. In particular, the characteristics of the device may specifically be or may comprise the capability of the device to have one or more relevant settings controlled. Specifically, the characteristics, such as the capability of the mobile device to have one or more relevant settings controlled, e.g., by a user's software running on the mobile device, may be evaluated by trying to control the one or more relevant settings and then determining a success of the control. As a simple example, the user's software may be used to send a command for individual values of the one or more relevant settings to equal preset reference values and may then, for example subsequently, compare the one or more relevant settings with said one or more reference values.

In order to indicate the mobile device's suitability for performing the analytical measurement based on a color formation reaction, the result of the comparison may be given in the at least one item of control information.

In particular, the comparison may be a qualitative or a quantitative comparison and may result in a binary or Boolean result such as "suited," specifically in case the individual values of the one or more relevant settings equal the reference values, or "not suited"/"unsuited," for example in case the values do not match. Thus, the at least one item of control information may particularly comprise Boolean information on the relevant settings of the mobile device and/or the camera being "controllable" or "uncontrollable." As a simple example, the at least one item of control information may show a "0" or "false" in case the at least one relevant setting is "uncontrollable," indicating that the mobile device is "not suited" or "unsuited" for performing the analytical measurement. Alternatively, the item of control information may show a "1" or "true" in case the relevant setting is "controllable," indicating that the mobile device is "suited" for performing the measurement. Different indications of the Boolean information on the relevant settings of the mobile device being controllable may also be possible, such as, for example, a reversed indication where "0" indicates "controllable" and "1" indicates "not controllable."

The term "providing at least one item of control information" as used herein is a broad term and is to be given its ordinary and customary meaning to a person of ordinary skill in the art and is not to be limited to a special or customized meaning. The term specifically may refer, without limitation, to an allocation of the at least one item of control information. In particular, the at least one item of control information may be provided in an electronic format, such as in an analogue and/or digital format. The at least one item of control information may be provided by transferring the item of control information to at least one of: an interface; a data storage device; a processing device; a software component, e.g., to a user's software running on the mobile device. The at least one item of control information may be provided as a data signal, specifically in form of an electronic signal. Thus, providing the at least one item of control information may for example refer to a process of supplying the at least one item of control information to the user's software running on the mobile device, specifically as a data signal, for example in form of an electrical signal, e.g., a binary signal.

Further, as will be outlined in further detail below, the method of evaluating the suitability of a mobile device for performing an analytical measurement may specifically be performed or supported by a computer or computer network, such as a computer or a computer network of a portable device, such as one or more of a notebook, a tablet or a cell phone such as a smartphone.

In a further aspect of this disclosure, a method of calibrating a mobile device for performing an analytical measurement based on a color formation reaction is disclosed, the mobile device having at least one camera. The method comprises the following method steps, which may be performed in the given order. Again, however, a different order may also be possible. Further, one, more than one or even all of the method steps may be performed once or repeatedly. Further, the method steps may be performed successively or, alternatively, two or more method steps may be performed in a timely overlapping fashion or even in parallel. The method may further comprise additional method steps which are not listed. In particular, the method of calibrating a mobile device for performing an analytical measurement based on a color formation reaction may also be referred to as calibration method.

The method of calibrating a mobile device for performing an analytical measurement based on a color formation reaction comprises the following steps:

i. evaluating the suitability of a mobile device for performing the analytical measurement by using the suitability method as disclosed in one or more of the embodiments above or as will further be disclosed in further optional detail below;

ii. if the item of control information indicates the mobile device being unsuitable for performing the analytical measurement, aborting the method;

iii. if the item of control information indicates the mobile device being suitable for performing the analytical measurement, performing the following steps:
   (1) providing at least one object having at least one predetermined reference color characteristic;
   (2) taking at least one reference image of at least part of the predetermined reference color characteristic by using the camera;
   (3) deriving at least one item of reference setting information pertaining to the relevant settings of the reference image; and
   (4) storing the at least one item of reference setting information derived in step (3), specifically in at least one database.

For further possible definitions of most of the terms used herein, reference may be made to the disclosure of the method of evaluating the suitability of the mobile device as disclosed above or as disclosed in further detail below. Specifically, since in step i., the suitability method is used for evaluating the suitability of the mobile device. As an example, step i. may make use of the at least one item of control information which, in particular, may be or may comprise digital information or Boolean information on whether the mobile device is "suited" or "not suited" for performing an analytical measurement. Depending on this control information, the method may branch between steps ii. and iii., wherein the inquiry regarding the suitability in step i. may be programmed, for example, as an "if . . . " routine, an "if . . . else . . . " routine or the like.

The term "reference object" as used herein is a broad term and is to be given its ordinary and customary meaning to a person of ordinary skill in the art and is not to be limited to a special or customized meaning. The term specifically may refer, without limitation, to an arbitrary object which comprises at least one predetermined reference color characteristic. As an example, the reference object may be or may comprise one or more of a predetermined visual reference color characteristic attached to, printed onto or integrated into an object such as: an optical test element or optical test strip; a test strip vial; a test element container, specifically a test strip container; a package for receiving at least one optical test element or optical test strip or a part thereof; a reference color card. The term "predetermined reference color characteristic" as used herein, may specifically refer, without limitation, to an arbitrary visual indicator, the qualities or features of which are known or predefined. As an example, the predetermined reference color characteristic may be or may comprise a reference field or area, specifically a reference color and/or grey scale field, an arbitrary area of a grey scale and/or a color, for example an inherent color of the at least one reference object. Specifically values of hue, lightness and saturation of the reference color characteristic may be known or may be predefined.

The term "item of reference setting information" as used herein is a broad term and is to be given its ordinary and customary meaning to a person of ordinary skill in the art and is not to be limited to a special or customized meaning. The term specifically may refer, without limitation, to an arbitrary item of information, e.g., one or more numerical values, which quantify at least one relevant setting of the reference image. Thus, as an example, the item of reference information may comprise information quantifying the relevant setting when taking the at least one reference image. Specifically the item of reference information may pertain to the relevant setting of the mobile device and/or the camera, in particular, referring to image processing configurations of the mobile device and/or camera.

As proposed herein, the step of evaluating the suitability of the mobile device and the step of calibrating the mobile device for performing the analytical measurement may be performed separately, wherein, once the suitability is determined, an arbitrary number of calibrations of the mobile device or, as will be outlined in further detail below, an arbitrary number of analytical measurements may be performed. Alternatively, however, the evaluation of the suitability of the mobile device in step i) may be repeated, e.g., after predetermined or determinable intervals or in case any changes are made to the mobile device. The user's software running on the mobile device, e.g., the software app, may prompt the user to perform method step i), e.g., by providing corresponding instructions on a display and/or as audio instructions. Specifically, however, step i) may be performed at least once before step iii) is performed, if at all. Step i) may be performed once before step iii) is performed at least once, or step i) may be performed once before step iii) is performed repeatedly.

In case the at least one item of control information indicates the mobile device being unsuitable or not suited for performing the analytical measurement, the method of calibrating a mobile device for performing an analytical measurement based on a color formation reaction may be aborted. This abortion, in particular step ii., may further comprise informing a user of the mobile device of the unsuitability of the mobile device for performing the analytical measurement. The information, as an example, may be provided in a usual form of providing information on a mobile device. Specifically, the information may be provided by using one or more of a visual, acoustic or haptic interface of the mobile device. For example, the unsuitability of the mobile device may be given to the user in a visual, haptic or acoustic form, such as on a display of the mobile device and/or as an audibly or haptically receivable signal, for example at least one beep or vibration.

Additionally or alternatively, in case the mobile device is determined as being unsuited for performing the analytical measurement, step ii) may also comprise blocking future attempts to perform the analytical measurement by using the mobile device. Thus, as an example, in case a user retries to start the software app on his or her mobile phone, a message such as "Sorry, mobile device not suited!" or the like may be displayed on a display, and the analytical measurement may be prevented.

Again, additionally or alternatively, step ii) may also comprise sending information on the mobile device being unsuited for performing the analytical measurement to a software download server, specifically in order to inform the software download server that this specific type of mobile device is unsuited, more specifically for preventing future offering of software download of software for analytical measurement for this specific type of mobile device. Thus, as an example, the download server may receive information regarding the unsuitability and may not provide analytical software download for this specific type of mobile device in the future.

In case the at least one item of control information indicates the mobile device being suited for performing the analytical measurement, at least steps (1) to (4) of the method of calibrating a mobile device for performing an analytical measurement may be performed, as indicated in step iii. Further, step iii. may comprise informing a user of the suitability of the mobile device for performing the analytical measurement, specifically by using one or more of a visual, acoustic or haptic user interface of the mobile device. In particular, the information of the mobile device being suitable for performing the analytical measurement may be provided to the user in a visual, haptic or acoustic form, such as on a display of the mobile device and/or as an audibly or haptically receivable signal, for example at least one beep or vibration.

As an example, the at least one reference object having the at least one predetermined reference color characteristic may be selected from the group consisting of: a test strip; a test strip vial; a container, specifically a test strip container; a package, e.g., a package for receiving at least one test strip or part thereof.

Further, in particular, the at least one predetermined reference color characteristic may be one or more of a reference color field, in particular a reference color field printed onto or otherwise attached to the at least one object, a grey scale and/or a color, specifically an inherent color of the at least one object.

Specifically, the item of reference setting information may for example be or may comprise one or more numerical values quantifying the relevant settings pertaining to image raw data processing steps carried out by the mobile device and/or camera when taking the image in step (2).

As an example, the item of setting information may specifically comprise at least one parameter relating to at least one of: a color space transformation and a tone mapping transformation, specifically by using a tone mapping curve, specifically relating to at least one image processing step, performed when taking the at least one reference image in step (2).

With respect to step (4), the at least one item of reference setting information may specifically be stored in at least one database, for example, in a data storage device such as in a memory of the mobile device and/or of the camera. However, the item of reference setting information may additionally or alternatively be stored on an external database or storage medium, such as in an online database or memory, for example in a cloud.

In particular, in step (4) the at least one item of reference setting information may be stored for use in a method of performing an analytical measurement based on a color formation reaction.

Further, as will be outlined in further detail below, the method of calibrating a mobile device for performing an analytical measurement may specifically be fully or partially supported and/or implemented by a computer or computer network, such as a computer or a computer network of a portable device, such as one or more of a notebook, a tablet or a cell phone such as a smartphone. In particular, at least steps i. and ii. or step i., iii. and (2) to (4) of the method of calibrating a mobile device for performing an analytical measurement based on a color formation reaction may be performed by using a computer or computer network.

In a further aspect of this disclosure, a method of performing an analytical measurement based on a color formation reaction in an optical test strip is disclosed, wherein a mobile device is used, the mobile device having a camera. The method comprises the following method steps, which may be performed in the given order. Again, however, a different order may also be possible. Further, one, more than one or even all method steps may be performed once or repeatedly. Further, the method steps may be performed successively or, alternatively, two or more method steps may be performed in a timely overlapping fashion or even in parallel. The method may further comprise additional method steps which are not listed. In particular, the method of performing an analytical measurement based on a color formation reaction may also be referred to as measurement method.

The method of performing an analytical measurement based on a color formation reaction in an optical test strip comprises the following steps:
A) verifying the suitability of the mobile device by performing at least one of
    evaluating the suitability of the mobile device by using the method of evaluating the suitability of the mobile device, specifically by using the suitability method as described above or as will further be described below; and
    checking if at least one item of reference setting information is stored according to step (4) of the method of calibrating a mobile device, specifically of the calibration method as described above or as will further be described below;
B) prompting a user to perform one or more of applying a sample, specifically a drop, of bodily fluid to an optical test strip and confirming said application;
C) waiting for a predetermined minimum amount of time; and
D) capturing at least one image of the optical test strip having the sample of bodily fluid applied thereto, wherein the at least one item of setting information is used to control at least one of the one or more relevant settings of the mobile device and/or of the camera.

The analytical measurement, specifically, may be an analytical measurement including a change of at least one optical property of an optical test strip, which change may be measured or determined visually by using the camera. Specifically, the analytical measurement may be or may comprise a color formation reaction in the presence of the at least one analyte to be determined. The term "color formation reaction" as used herein is a broad term and is to be given its ordinary and customary meaning to a person of ordinary skill in the art and is not to be limited to a special or customized meaning. The term specifically may refer, without limitation, to a chemical, biological or physical reaction during which a color, specifically a reflectance, of at least one element involved in the reaction, changes with the progress of the reaction.

The term "optical test strip" as used herein is a broad term and is to be given its ordinary and customary meaning to a person of ordinary skill in the art and is not to be limited to a special or customized meaning. The term specifically may refer, without limitation, to an arbitrary element or device configured for performing a color-change detection reaction. The optical test strip may also be referred to as test strip or test element, wherein all three terms may refer to the same element. The optical test strip may particularly have a test field containing at least one test chemical for detecting at least one analyte. The optical test strip, as an example, may comprise at least one substrate, such as at least one carrier, with the at least one test field applied thereto or integrated therein. As an example, the at least one carrier may be strip-shaped, thereby rendering the test element a test strip. These test strips are generally widely in use and available. One test strip may carry a single test field or a plurality of test fields having identical or different test chemicals comprised therein.

As proposed herein, the step of evaluating the suitability of the mobile device and the actual step of performing the analytical measurement may be performed separately, wherein, once the suitability is determined, an arbitrary number of analytical measurements based on a color formation reaction may be performed using the mobile device. Alternatively, however, the evaluation of the suitability of the mobile device may be repeated, e.g., after predetermined or determinable intervals or in case any changes are made to the mobile device.

In particular, step A) may be performed at least once before step B) is performed. Thus, as an example, when performing the analytical measurement a verification of the suitability of the mobile device may be performed before the user's software running on the mobile device, e.g., the software app, may prompt the user to perform or confirm application of the sample according to method step B), e.g., by providing corresponding instructions on a display and/or as audio instructions. As an example, the suitability of the mobile device may be verified by one or both of performing the suitability method or checking performance of step (4) of the calibration method. Thus, for possible definitions of terms and possible embodiments, reference may be made to the description given above or described in further detail below.

As an example, when performing the measurement method, firstly the suitability of the mobile device may be verified. Specifically as indicated by step A) of the method, the suitability may be verified by performing by one or both of the options given above. In particular, it may be verified that an internal image processing of the mobile device is controllable. Subsequently, step B) may be performed, e.g., the user may be prompted to apply a sample, specifically a drop of bodily fluid, to an optical test strip. After performing step C), step D) may be performed, e.g., at least one image of the optical test strip having the sample applied thereto may be captured, wherein the at least one item of setting information may be used to control at least one of the one or more relevant settings of the mobile device. Thus, as an example, when performing step D) of the measurement method, the item of setting information may equal the item of reference setting information derived in step (3) of the calibration method. In particular, the at least one item of setting information pertaining to relevant settings of the mobile device when performing step D) may be set to equal the item of reference setting information derived in step (3) of the calibration method.

The method of performing an analytical measurement based on a color formation reaction may further comprise step E) of determining at least one concentration of the analyte in the sample of bodily fluid applied to the optical test strip. In particular, the at least one concentration of the analyte in the sample of bodily fluid may for example be determined by assessing a color formation reaction in an optical test strip, such as for example a color formation reaction of the optical test strip depending on a concentration of the analyte in the sample, specifically the color formation reaction of a test field in an optical test strip.

As an example, in step E), image data such as a measured value referring to at least one color within the image may be generated by image acquisition of an optical test strip. An average of the measured value, e.g., an average color value, such as a color average value of a test field of the optical test strip, may be determined and may further be set in relation with a reference color, such as with a value of a known or predetermined color, for example a white color of the test strip, e.g., a stripe white. Specifically, in order to determine the analyte concentration, the average color of the test field of the optical test strip, in particular, the average of the measured value referring to the color of the test field of the optical test strip, may be set in relation to the value referring to the reference color.

In particular, step C) of waiting for a predetermined minimum amount of time, may specifically comprise waiting for at least 5 s. Thus, as an example, the method of performing an analytical measurement based on a color formation reaction in an optical test strip may comprise waiting for 5 s after application of the sample to the optical test strip of step B), before the capturing of the at least one image of step D) of the method.

Further, as an example, in step D) at least one image of the optical test strip as well as a reference object, such as for example a reference color card, may be captured. In particular, the at least one concentration of the analyte in the sample of bodily fluid applied to the optical test strip may be determined by using the image of the reference object, specifically of the reference color card. Specifically, the average of the measured value of the rest field of the optical test strip may be set in relation with the reference color characteristic of the reference object, e.g., of the reference color card. Thus, as an example, in step D) a combined image of the optical test strip and the reference object, e.g., the reference color card, may be captured.

Further, as will be outlined in further detail below, the method of performing an analytical measurement based on a color formation reaction in an optical test strip may specifically be performed or supported by a computer or computer network, such as a computer or a computer network of a portable device, such as one or more of a notebook, a tablet or a cell phone such as a smartphone.

In a further aspect, a suitability computer program, specifically a smartphone app, including computer-executable instructions for performing the method of evaluating the suitability of a mobile device having at least one camera is disclosed. The suitability computer program is configured for performing the method of evaluating the suitability of a mobile device as described above or as will further be described below, when the program is executed on a computer or a computer network, specifically on a processor of the mobile device having at least one camera. In particular, the suitability computer program may be configured for performing the suitability method when executed on the computer or computer network. Thus, the suitability computer program may specifically be configured for performing at least steps a) and b) or steps a) and c) of the suitability method as described above, when executed on the computer or computer network.

Again, for possible definitions of terms and possible embodiments, reference may be made to the description given above or described in further detail below.

Specifically, the suitability computer program may be stored on a computer-readable data carrier. Thus, further disclosed and proposed herein is a data carrier having a data structure stored thereon, which, after loading into a computer or computer network, such as into a working memory or main memory of the computer or computer network, may execute the suitability method according to one or more of the embodiments disclosed herein.

In a further aspect, a calibration computer program, specifically a smartphone app, including computer-executable instructions for performing the method of calibrating a mobile device is disclosed. The calibration computer program is configured for performing the calibration method as described above or as will further be described below, when the program is executed on a computer or a computer network, specifically on a processor of a mobile device having at least one camera. In particular, the calibration computer program may be configured for performing the calibration method when executed on the computer or computer network. Thus, the calibration computer program may specifically be configured for performing at least steps i. and ii. or at least steps i. and iii., particularly steps i. and iii. as well as steps (2) to (4), of the calibration method as described above, when executed on the computer or computer network.

Again, for possible definitions of terms and possible embodiments, reference may be made to the description given above or described in further detail below.

Specifically, the calibration computer program may be stored on a computer-readable data carrier. Thus, further disclosed and proposed herein is a data carrier having a data structure stored thereon, which, after loading into a computer or computer network, such as into a working memory or main memory of the computer or computer network, specifically into a processor of a mobile device having at least one camera, may execute the calibration method according to one or more of the embodiments disclosed herein.

In a further aspect, a measurement computer program, specifically a smartphone app, including computer-executable instructions for performing the method of performing an analytical measurement based on a color formation reaction is disclosed. The measurement computer program is configured for performing the method of performing the analytical measurement based on a color formation reaction as described above or as will further be described below, when the program is executed on a computer or a computer network, specifically on a processor of a mobile device having at least one camera. In particular, the measurement computer program may be configured for performing the measurement method when executed on the computer or computer network. Thus, the measurement computer program may specifically be configured for performing at least steps A) to D) of the measurement method as described above, when executed on a computer or computer network.

Again, for possible definitions of terms and possible embodiments, reference may be made to the description given above or described in further detail below.

Specifically, the measurement computer program may be stored on a computer-readable data carrier. Thus, further disclosed and proposed herein is a data carrier having a data structure stored thereon, which, after loading into a computer or computer network, such as into a working memory or main memory of the computer or computer network, specifically into a processor of a mobile device having at least one camera, may execute the measurement method according to one or more of the embodiments disclosed herein.

In a further aspect, a mobile device is disclosed. The mobile device has at least one camera and at least one processor with software being configured for performing one or more of:
 the method of evaluating the suitability of a mobile device for performing an analytical measurement based on a color formation reaction as described above or as will further be described below;
 the method of calibrating a mobile device for performing an analytical measurement based on a color formation reaction as described above or as will further be described below; and
 the method of performing an analytical measurement based on a color formation reaction in an optical test strip by using a mobile device having a camera as described above or as will further be described below.

Again, for possible definitions of terms and possible embodiments, reference may be made to the description given above or described in further detail below.

In a further aspect, a kit is disclosed. The kit comprises the mobile device as described above or as will further be described below. The kit further comprises at least one reference object having at least one predetermined reference color characteristic, wherein the kit further comprises at least one optical test strip. As described above, the reference object itself may be or may comprise the optical test strip. Thus, the at least one reference object and the at least one optical test strip comprised by the kit may for example be combined in one optical test strip having at least one predetermined reference color characteristic.

Again, for possible definitions of terms and possible embodiments, reference may be made to the description given above or described in further detail below.

The term "kit" as used herein is a broad term and is to be given its ordinary and customary meaning to a person of ordinary skill in the art and is not to be limited to a special or customized meaning. The term specifically may refer, without limitation, to an assembly of a plurality of components, wherein the components each may function and may be handled independently from each other, wherein the components of the kit may interact to perform a common function.

The methods, computer programs and devices as disclosed herein may provide a large number of advantages over known methods, computer programs and devices. Thus, in particular, a process of performing an analytical measurement as suggested in this disclosure may be less time-consuming, compared to other processes known in the art. Specifically, this disclosure may evaluate a general aptitude of a mobile device used for performing the measurement. An established aptitude or suitability of the mobile device may be valid for one, more than one, or even all subsequent measurements, such that, as an example, when performing the measurement itself, merely a verification of the suitability may be necessary. Thus, this disclosure may need less time for performing an analytical measurement compared to prior art approaches.

Further, this disclosure may simplify the process of performing the analytical measurement for a user. Specifically, once a general suitability of the mobile device may be established the process of performing the analytical measurement may be simpler than state-of-the-art measurements. In particular, using a suitable mobile device, this disclosure may simplify the process of performing a blood glucose measurement for a user. When using a suitable mobile device, the process of performing the blood glucose measurement may, particularly, need less time than state-of-the-art processes.

This disclosure may only allow a suitable mobile device to be used for performing the analytical measurement based on a color formation reaction. Particularly, this disclosure may only allow a use of a computer program, specifically a measurement computer program, including computer-executable instructions for performing the analytical measurement based on a color formation reaction, in conjunction with a mobile device capable of having one or more of its relevant settings controlled by a user's software running on the mobile device. Thereby, this disclosure may improve safety of using a mobile device for performing the analytical measurement. In particular, the safety of a valid result, e.g., a validity of a result of the analytical measurement, may be ensured by this disclosure.

Summarizing and without excluding further possible embodiments, the following embodiments may be envisaged:

Embodiment 1: A method of evaluating the suitability of a mobile device for performing an analytical measurement based on a color formation reaction, the mobile device having at least one camera, the method comprising:
  a) evaluating the capability of the mobile device to have one or more relevant settings of the mobile device controlled by a user's software running on the mobile device, the relevant settings pertaining to image raw data processing steps to be carried out by the mobile device, wherein the relevant settings include at least one of: a color space transformation and a tone mapping transformation, specifically by using a tone mapping curve;
  b) if the evaluation in step a) indicates that the mobile device is capable of having the one or more relevant settings controlled by the user's software, providing at least one item of control information, specifically to one or more of the mobile device, the user or the user's software running on the mobile device, the at least one item of control information indicating that the mobile device is suitable for performing the analytical measurement; and
  c) if the evaluation in step a) indicates that the mobile device is not capable of having the one or more relevant settings controlled by the user's software, providing at least one item of control information, specifically to one or more of the mobile device, the user or the user's software running on the mobile device, the at least one item of control information indicating that the mobile device is unsuitable for performing the analytical measurement.

Embodiment 2: The method according to the preceding embodiment, wherein the at least one item of control information comprises Boolean information on the relevant settings of the mobile device and/or camera being "controllable" or "uncontrollable."

Embodiment 3: The method according to any one of the preceding embodiments, wherein the method of evaluating the suitability of a mobile device for performing an analytical measurement based on a color formation reaction is performed by using a computer or computer network.

Embodiment 4: A method of calibrating a mobile device for performing an analytical measurement based on a color formation reaction, the mobile device having at least one camera, the method comprising:
  i. evaluating the suitability of a mobile device for performing the analytical measurement by using the method according to any one of the preceding embodiments;
  ii. if the item of control information indicates the mobile device being unsuitable for performing the analytical measurement, aborting the method;
  iii. if the item of control information indicates the mobile device being suitable for performing the analytical measurement, performing the following steps:
    (1) providing at least one reference object having at least one predetermined reference color characteristic;
    (2) taking at least one reference image of at least part of the predetermined reference color characteristic by using the camera;
    (3) deriving at least one item of reference setting information pertaining to the relevant settings of the reference image; and
    (4) storing the at least one item of reference setting information derived in step (3), specifically in at least one database.

Embodiment 5: The method according to the preceding embodiment, wherein step ii. further comprises informing a user of the mobile device of the unsuitability of the mobile device for performing the analytical measurement, specifically by using one or more of a visual, acoustic or haptic user interface of the mobile device.

Embodiment 6: The method according to any one of the two preceding embodiments, wherein step iii. further comprises informing a user of the suitability of the mobile device for performing the analytical measurement, specifically by using one or more of a visual, acoustic or haptic user interface of the mobile device.

Embodiment 7: The method according to any one of the three preceding embodiments, wherein the at least one reference object having the at least one predetermined reference color characteristic is selected from the group consisting of: a test strip; a test strip vial; a container, specifically a test strip container; a package, e.g., a package for receiving at least one test strip or part thereof; a reference color card.

Embodiment 8: The method according to any one of the four preceding embodiments, wherein the at least one predetermined reference color characteristic is one or more of a reference color field, in particular a reference color field printed onto or otherwise attached to the at least one object, a grey scale and/or a color, specifically an inherent color of the at least one object.

Embodiment 9: The method according to any one of the five preceding embodiments, wherein the item of setting information comprises at least one parameter relating to at least one of: a color space transformation and a tone mapping transformation, specifically by using a tone mapping curve, specifically relating to at least one image processing step, performed when taking the at least one reference image in step (2).

Embodiment 10: The method according to any one of the six preceding embodiments, wherein in step (4) the at least one item of reference setting information is stored for use in a method of performing an analytical measurement based on a color formation reaction.

Embodiment 11: The method according to any one of the seven preceding embodiments, wherein the method of calibrating a mobile device for performing an analytical measurement based on a color formation reaction is performed by using a computer or computer network.

Embodiment 12: A method of performing an analytical measurement based on a color formation reaction in an optical test strip by using a mobile device having a camera, comprising:
  A) verifying the suitability of the mobile device by performing at least one of
    evaluating the suitability of the mobile device by using the method according to any one of the preceding embodiments referring to a method of evaluating the suitability of the mobile device; and
    checking if at least one item of reference setting information is stored according to step (4) of the method of calibrating a mobile device according to any one of the preceding embodiments referring to a method of calibrating a mobile device;
  B) prompting a user to perform one or more of applying a sample, specifically a drop, of bodily fluid to an optical test strip and confirming application of a sample, specifically a drop, of bodily fluid to an optical test strip;

C) waiting for a predetermined minimum amount of time; and

D) capturing at least one image of the optical test strip having the sample of bodily fluid applied thereto, wherein the at least one item of setting information is used to control at least one of the one or more relevant settings of the mobile device.

Embodiment 13: The method according to the preceding embodiment, wherein step A) is performed at least once before step B) is performed.

Embodiment 14: The method according to any one of the two preceding embodiments, wherein the method further comprises step E) of determining at least one concentration of the analyte in the sample of bodily fluid applied to the optical test strip.

Embodiment 15: The method according to any one of the three preceding embodiments, wherein method step C) comprises waiting for at least 5 s.

Embodiment 16: The method according to any one of the four preceding embodiments, wherein the method of performing an analytical measurement based on a color formation reaction in an optical test strip is performed by using a computer or computer network.

Embodiment 17: A suitability computer program, specifically a smartphone app, including computer-executable instructions for performing the method of evaluating the suitability of a mobile device having at least one camera for performing an analytical measurement based on a color formation reaction according to any one of the preceding embodiments referring to a method of evaluating the suitability of a mobile device when the program is executed on a computer or a computer network, specifically on a processor of a mobile device having at least one camera.

Embodiment 18: A calibration computer program, specifically a smartphone app, including computer-executable instructions for performing the method of calibration a mobile device according to any one of the preceding embodiments referring to a method of calibrating a mobile device when the program is executed on a computer or a computer network, specifically on a processor of a mobile device having at least one camera.

Embodiment 19: A measurement computer program, specifically a smartphone app, including computer-executable instructions for performing the method of performing an analytical measurement based on a color formation reaction according to any one of the preceding embodiments referring to a method of performing an analytical measurement when the program is executed on a computer or a computer network, specifically on a processor of a mobile device having at least one camera.

Embodiment 20: A mobile device having at least one camera, the mobile device having at least one processor with software being configured for performing one or more of:

the method of evaluating the suitability of a mobile device for performing an analytical measurement based on a color formation reaction as claimed in any one of the preceding embodiments referring to a method of evaluating the suitability of a mobile device;

the method of calibrating a mobile device for performing an analytical measurement based on a color formation reaction as claimed in any one of the preceding embodiments referring to a method of calibrating a mobile device; and the method of performing an analytical measurement based on a color formation reaction in an optical test strip by using a mobile device having a camera as claimed in any one of the preceding embodiments referring to a method of performing an analytical measurement.

Embodiment 21: A kit, comprising the mobile device according to the preceding embodiment, further comprising at least one reference object having at least one predetermined reference color characteristic, the kit further comprising at least one optical test strip.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
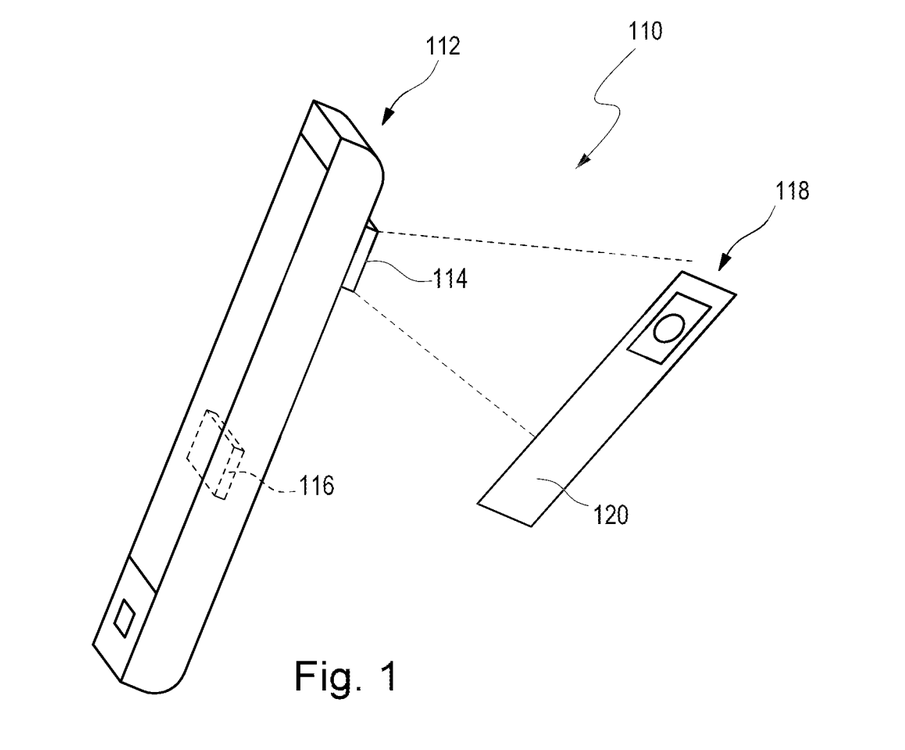
FIG. 1 shows a perspective view of an embodiment of a kit and a mobile device.

In FIG. 1 a kit 110 for performing an analytical measurement is shown in a perspective view. The kit 110 comprises at least one mobile device 112 having at least one camera 114 and at least one processor 116 with software. The kit 110 further has at least one reference object 118 having at least one predetermined reference color characteristic and at least one optical test strip 120. In particular, the reference object 118 and the optical test strip 120 may be combined in one object, thus, as illustrated in the Figure, the reference object 118 may be or may comprise the optical test strip 120.

Figure 2:
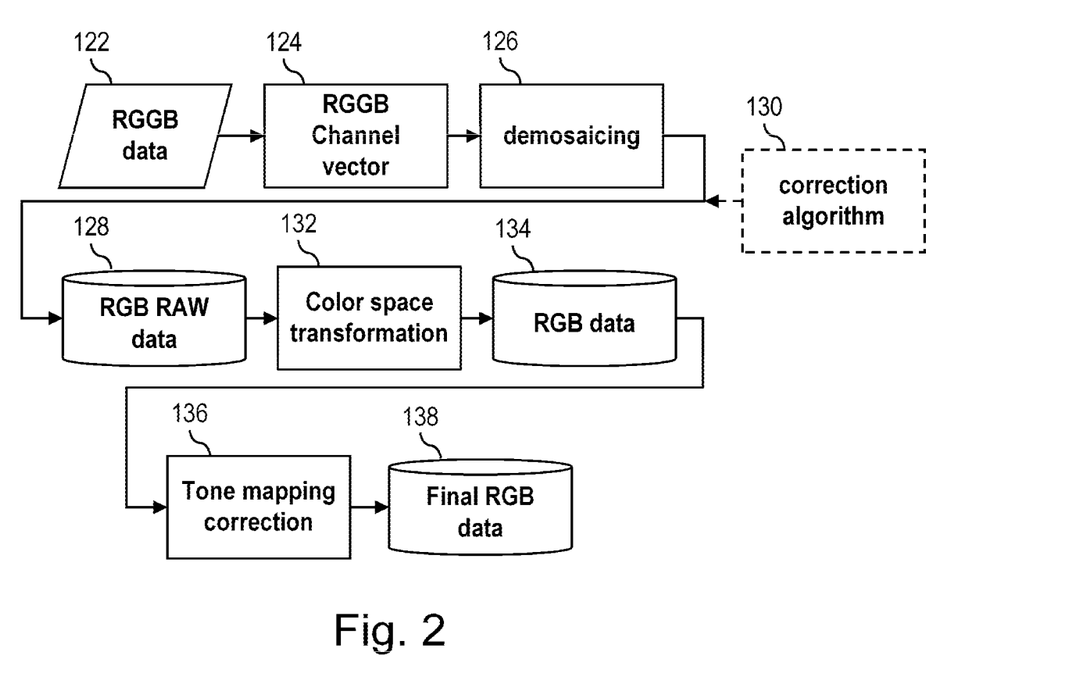
FIG. 2 shows a flow chart of an image processing chain.

FIG. 2 illustrates an exemplary embodiment of a flow chart of an image processing chain of the mobile device 112. In particular, image processing routines of the mobile device 116 may for example be optimized for generating images that are as attractive to a human eye as possible. Specifically, a variety of algorithms, e.g., image optimization algorithms, may be used for this purpose. For example, such algorithms may comprise changing image data, specifically four dimensional image data, such as information on the image in R, G, G, and B, channels, e.g., RGGB data 122, into an RGGB Channel vector 124 and performing an algorithm of demosaicing 126 to generate three dimensional RGB RAW data 128 of the image. Further, various correction algorithms 130, such as hot pixel correction, noise reduction, shading correction and geometric correction, may additionally be performed when generating the RGB RAW data 128. Subsequently, for example, a color space transformation 132 may be performed for generating RGB data 134 from the RGB RAW data 128. Further, tone mapping correction 136 may be performed to generate final RGB data 138 from the RGB data 134. However, these algorithms may, for example, change image information, e.g., image pixel information, in a non-linear fashion and may therefore change the image information into being unsuitable for measurement tasks such as performing an analyte measurement. In particular, the steps of color space transformation 132 and tone mapping correction 136 may, for example, lead to unwanted color mixtures and an introduction of non-linearities into image data. Thus, not all mobile devices 112 may be suited for performing an analytical measurement based on a color formation reaction.

Figure 3:
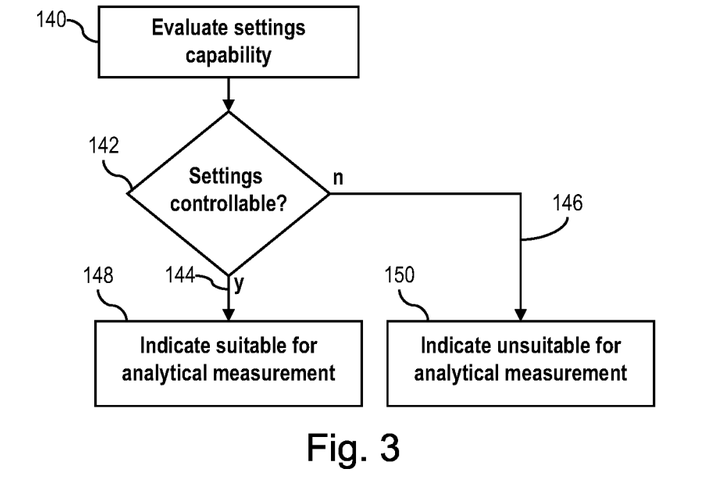
FIG. 3 shows a flow chart of a method of evaluating the suitability of a mobile device.

FIG. 3 shows an embodiment of a flow chart of a method of evaluating the suitability of a mobile device 112 having at least one camera 114. The method of evaluating the suitability of the mobile device 112, also referred to as suitability method, comprises step a) (indicated with reference number 140) evaluating the capability of the mobile device 112 to have one or more relevant settings of the mobile device 112 controlled by a user's software running on the mobile device 112, the relevant settings pertaining to image raw data processing steps to be carried out by the mobile device 112, wherein the relevant settings include at least one of a color space transformation 132 and a tone mapping correction 136. Further, the suitability method may comprise a branching point 142 indicating a condition query, such as deciding between a first branch 144 indicating that the relevant settings of the mobile device 112 can ("y") be controlled by the user's software running on the mobile device 112 the mobile device 112 and a second branch 146 indicating that the relevant settings of the mobile device 112 cannot ("n") be controlled. The first branch 144 indicates the relevant settings of the mobile device 112 being controllable by the user's software, thus the branch may lead to step b) (indicated with reference number 148) if the evaluation in step a) indicates that the mobile device 112 is capable of having the one or more relevant settings controlled by the user's software, providing at least one item of control information indicating that the mobile device 112 is suitable for performing the analytical measurement. The second branch 146 indicates the relevant settings of the mobile device 112 being uncontrollable by the user's software, thus the branch may lead to step c) (indicated with reference number 150) if the evaluation in step a) indicates that the mobile device is not capable of having the one or more relevant settings controlled by the user's software, providing at least one item of control information indicating that the mobile device is unsuitable for performing the analytical measurement.

Figure 4:
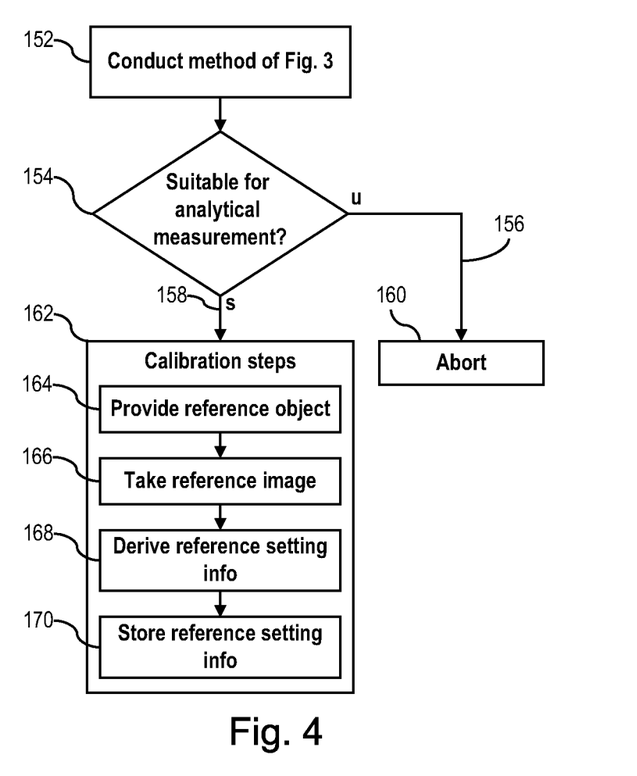
FIGS. 4 and 5 show flow charts of a method of calibrating a mobile device.

In FIG. 4, an embodiment of a flow chart of a method of calibrating a mobile device 112 for performing an analytical measurement based on a color formation reaction is illustrated. The method of calibrating a mobile device 112 for performing an analytical measurement, also referred to as calibration method, comprises step i. (indicated with reference number 152) evaluating the suitability of a mobile device 112 for performing the analytical measurement by using the suitability method as described above. Further, the calibration method may comprise a branching point 154 indicating a condition query, such as deciding between a first branch 156 indicating the mobile device 112 being "not suitable" or "unsuitable" ("u") for performing the analytical measurement and a second branch 158 indicating the mobile device 112 being "suitable" ("s") for performing the analytical measurement. Thus, the first branch 156 may lead to step ii. (indicated with reference number 160) if the item of control information indicates the mobile device 112 being unsuitable for performing the analytical measurement, aborting the method. However, the second branch 158 may lead to step iii. (indicated with reference number 162) if the item of control information indicates the mobile device being suitable for performing the analytical measurement, performing the following steps:

(1) (indicated with reference number 164) providing at least one reference object 118 having at least one predetermined reference color characteristic;

(2) (indicated with reference number 166) taking at least one reference image of at least part of the predetermined reference color characteristic by using the camera;

(3) (indicated with reference number 168) deriving at least one item of reference setting information pertaining to the relevant settings of the reference image; and (4) (indicated with reference number 170) storing the at least one item of reference setting information derived in step (3).

Figure 5:
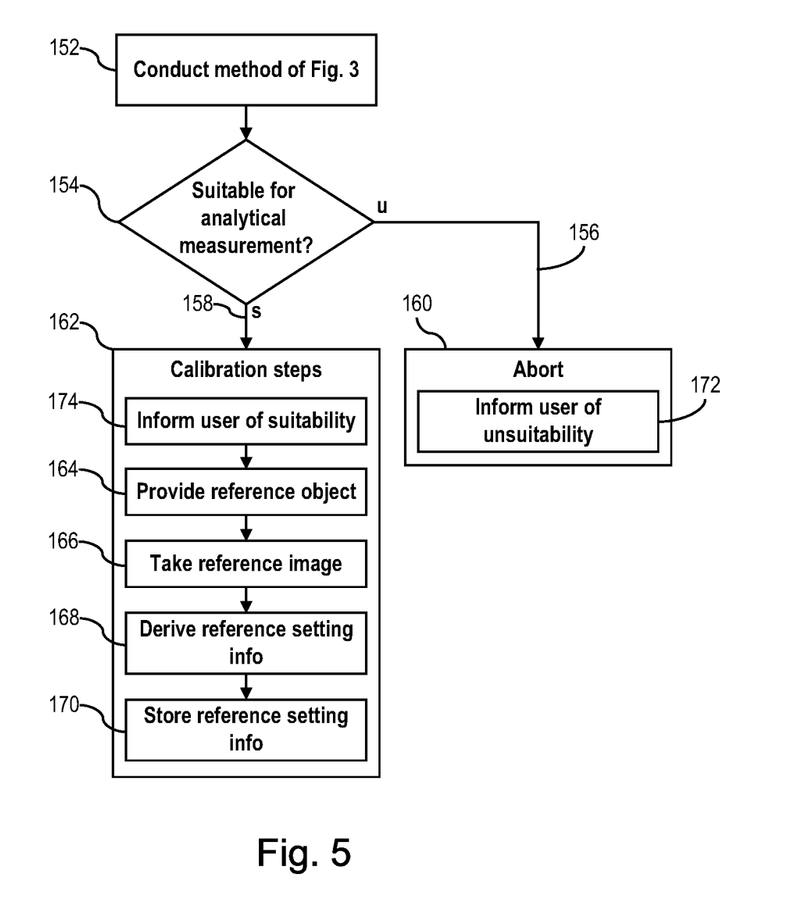

Further, as indicated in FIG. 5, step ii. of the calibration method may further comprise at least one substep (indicated with reference number 172) informing a user of the mobile device 112 of the unsuitability of the mobile device 112 for performing the analytical measurement, specifically by using one or more of a visual, acoustic or haptic user interface of the mobile device 112. In particular, step iii. of the calibration method may further comprise at least one further substep (indicated with reference number 174) informing a user of the mobile device 112 of the suitability of the mobile device 112 for performing the analytical measurement, specifically by using one or more of a visual, acoustic or haptic user interface of the mobile device 112.

Figure 6:
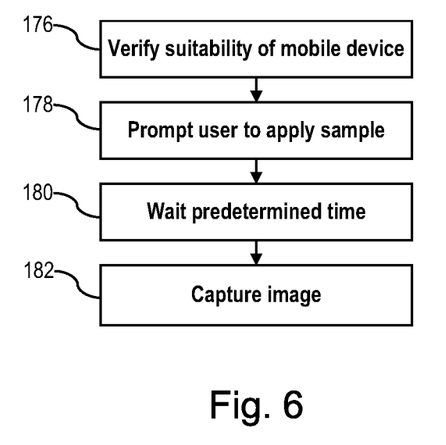
FIGS. 6 and 7 show flow charts of a method of performing an analytical measurement.

In FIG. 6, an embodiment of a flow chart of a method of performing an analytical measurement is shown. The method of a method of performing an analytical measurement, also referred to as measurement method, comprises the following steps:

A) (indicated with reference number 176) verifying the suitability of the mobile device 112 by performing at least one of evaluating the suitability of the mobile device 112 by using the method of evaluating the suitability of the mobile device 112 as, for example, illustrated in FIG. 3; and checking if at least one item of reference setting information is stored according to step (4) of the method of calibrating a mobile device 112 as, for example illustrated in FIGS. 4 and 5;

B) (indicated with reference number 178) prompting a user to perform one or more of applying a sample, specifically a drop, of bodily fluid to an optical test strip and/or prompting the user to confirming application of a sample, specifically a drop, of bodily fluid to an optical test strip;

C) (indicated with reference number 180) waiting for a predetermined minimum amount of time; and D) (indicated with reference number 182) capturing at least one image of the optical test strip having the sample of bodily fluid applied thereto, wherein the at least one item of setting information is used to control at least one of the one or more relevant settings of the mobile device.

Figure 7:
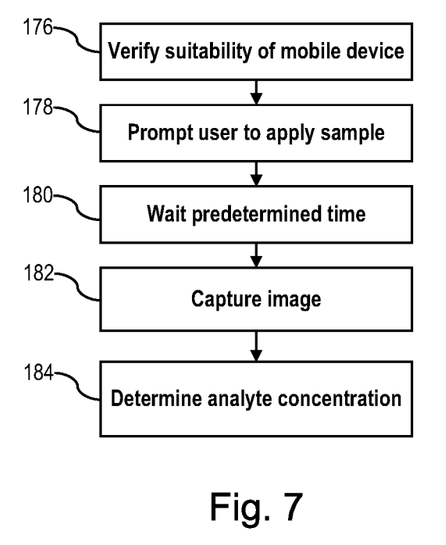

In particular, step A) 176 may be performed at least once before step B) 178 may be performed. Further, as indicated in FIG. 7, the method of performing an analytical measurement, e.g., the measurement method, may additionally comprise step E) (indicated with reference number 184) determining at least one concentration of the analyte in the sample of bodily fluid applied to the optical test strip.

Figure 8:
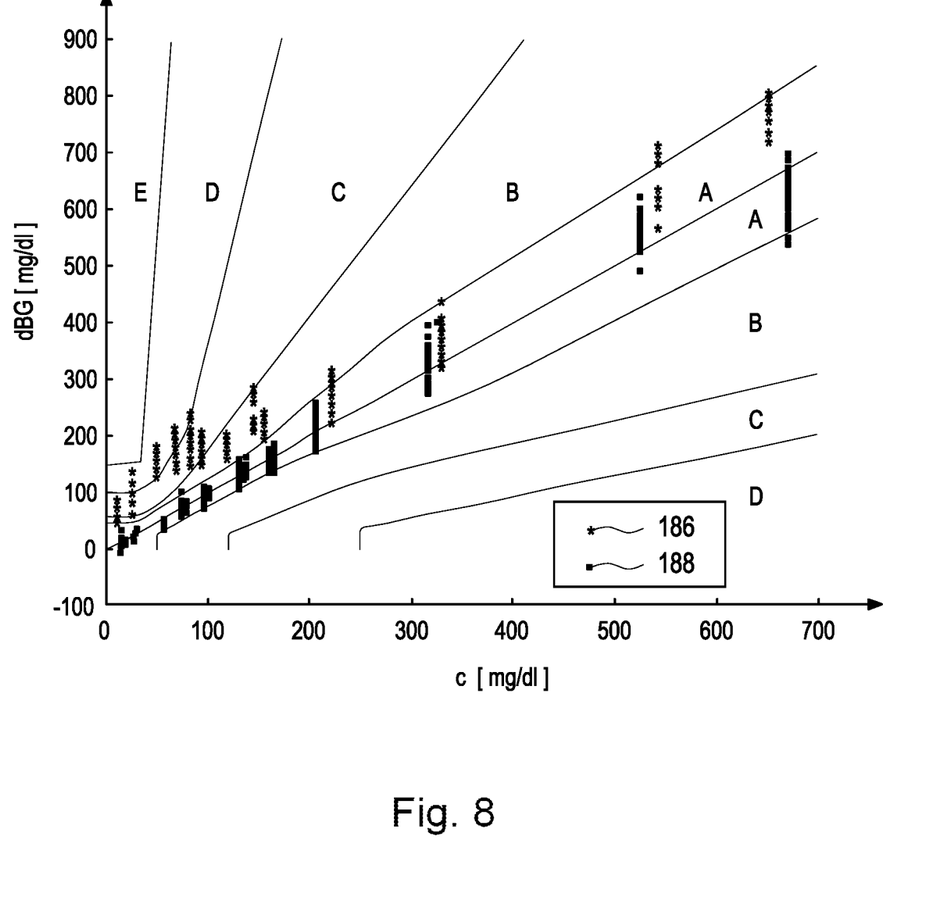
FIG. 8 shows an embodiment of a diagram indicating a relationship between actual analyte concentrations and determined analyte concentrations showing a difference between using common methods and devices and using present methods and devices for performing the analytical measurement.

FIG. 8 illustrates an embodiment of a diagram indicating a relationship between actual analyte concentrations and determined analyte concentrations showing a difference between using common methods and devices and using present methods and devices for performing the analytical measurement. The analyte referred to in FIG. 8 is blood glucose, thus the diagram illustrates blood glucose concentrations. Specifically, the diagram illustrated in FIG. 8 indicates a relationship between actual blood glucose values (c) and determined blood glucose values (dBG). Two measurement series or sequences are illustrated. The data points of the first measurement sequence 186 are illustrated in the diagram using a "*" symbol and refer to analyte concentrations determined by using common methods and devices. The data points of the second measurement sequence 188 is illustrated in the diagram using a "." symbol and refers to analyte concentrations determined by using present methods and devices, specifically methods and devices as disclosed herein. In particular, a comparison of the data points of the first measurement sequence 186 and the data points of the second measurement sequence 188 shows an improved accuracy when using present methods and devices as opposed to using common approaches for determining the blood glucose concentration. Specifically, as illustrated in the diagram, a lower scattering of determined blood glucose values may be achieved when using present methods and devices.

Further, FIG. 8 show regions A to E of an Error-Grid-Analysis, specifically regions A to E of the Parkes Error Grid, quantifying clinical accuracy of a determined blood glucose concentration compared to an actual blood glucose concentration. For more information on the Error-Grid-Analysis reference may be made to Clarke WL, Cox D, Gonder-Frederick LA, Carter W, Pohl SL: Evaluating clinical accuracy of systems for self-monitoring of blood glucose. Diabetes Care 10:622-628, 1987.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 kit
112 mobile device
114 camera
116 processor
118 reference object
120 optical test strip
122 RGGB data
124 RGGB Channel vector
126 demosaicing
128 RGB RAW data
130 correction algorithm
132 color space transformation
134 RGB data
136 tone mapping correction
138 final RGB data
140 step a)
142 branching point
144 first branch
146 second branch
148 step b)
150 step c)
152 step i.
154 branching point
156 first branch
158 second branch
160 step ii.
162 step iii.
164 step (1)
166 step (2)
168 step (3)
170 step (4)
172 substep: informing a user of the mobile device of the unsuitability of the mobile device for performing the analytical measurement
174 substep: informing a user of the mobile device of the suitability of the mobile device for performing the analytical measurement
176 step A)
178 step B)
180 step C)
182 step D)
184 step E)
186 data points of first measurement sequence
188 data points of second measurement sequence

What is claimed is:

1. A method of calibrating a mobile device having a camera for performing an analytical measurement based on a color formation reaction, the method comprising:
    a) evaluating the capability of the mobile device to have one or more relevant settings of the mobile device controlled by software running on the mobile device, the relevant settings pertaining to image raw data processing steps to be carried out by the mobile device, wherein the relevant settings include at least one of: a color space transformation and a tone mapping transformation;
    b) when the evaluation of step a) indicates that the mobile device is capable of having the one or more relevant settings controlled by the software, providing at least one item of control information indicating that the mobile device is suitable for performing the analytical measurement and performing the following steps:
        (1) providing a reference object having a predetermined reference color characteristic;
        (2) taking a reference image of at least part of the predetermined reference color characteristic using the camera;
        (3) deriving an item of reference setting information pertaining to the relevant settings of the reference image; and
        (4) storing the item of reference setting information derived in step (3).

2. The method according to claim 1, wherein the reference object is selected from the group consisting of a test strip, a test strip vial, a container, a package and a reference color card.

3. The method according to claim 1, wherein the item of setting information comprises at least one parameter relating to at least one of: a color space transformation and a tone mapping transformation.

4. The method of claim 1, further comprising:
A) checking whether reference setting information pertaining to relevant settings of a reference image is stored in memory of the mobile device;
B) prompting a user to perform one or more of applying a sample of bodily fluid to an optical test strip and confirming application of a sample of bodily fluid to an optical test strip;
C) waiting a predetermined minimum amount of time; and
D) capturing at least one image of the optical test strip having the sample of bodily fluid applied thereto, wherein the reference setting information is used to control one or more relevant settings of the mobile device.

5. The method according to claim 4, wherein step A) is performed at least once before step B) is performed.

6. The method according to claim 4, wherein the method further comprises step E) of determining at least one concentration of the analyte in the sample of bodily fluid applied to the optical test strip.

7. The method according to claim 4, wherein step C) comprises waiting for at least 5 seconds.

8. A non-transitory computer readable medium having stored thereon computer-executable instructions for performing the method of claim 1.

9. A mobile device having at least one camera and at least one processor having stored thereon computer-executable instructions for performing the method of claim 1.

10. The mobile device according to claim 9 and further comprising at least one reference object having at least one predetermined reference color characteristic and at least one optical test strip.

11. The method of calibrating a mobile device according to claim 1, wherein when the evaluation in step a) indicates that the mobile device is not capable of having the one or more relevant settings controlled by the software, providing at least one item of control information indicating that the mobile device is unsuitable for performing the analytical measurement.

12. A method of performing an analytical measurement based on a color formation reaction in an optical test strip by using a mobile device having a camera, comprising:
verifying suitability of the mobile device by performing by performing the following steps:
a) evaluating the capability of the mobile device to have one or more relevant settings of the mobile device controlled by a user's software running on the mobile device, the relevant settings pertaining to image raw data processing steps to be carried out by the mobile device, wherein the relevant settings include at least one of: a color space transformation and a tone mapping transformation;
b) if the evaluation in step a) indicates that the mobile device is capable of having the one or more relevant settings controlled by the user's software, providing at least one item of control information, the at least one item of control information indicating that the mobile device is suitable for performing the analytical measurement; and
c) if the evaluation in step a) indicates that the mobile device is not capable of having the one or more relevant settings controlled by the user's software, providing at least one item of control information, the at least one item of control information indicating that the mobile device is unsuitable for performing the analytical measurement,
wherein the suitability is a property of the mobile device for performing one or more predetermined functions, wherein the suitability is qualified or quantified by using one or more characteristics of the mobile device, wherein the characteristics of the mobile device comprise the capability of the mobile device to have the one or more relevant settings controlled;
capturing at least one image of a reference object to determine an item of reference setting information, wherein the item of reference setting information is used to control at least one of the one or more relevant settings of the mobile device.

13. The method of performing an analytical measurement according to claim 12, further comprising:
prompting a user to perform one or more of applying a sample of bodily fluid to an optical test strip and confirming application of a sample of bodily fluid to an optical test strip;
waiting for a predetermined minimum amount of time; and
capturing at least one image of the optical test strip having the sample of bodily fluid applied thereto.

14. A method of evaluating the suitability of a mobile device for performing an analytical measurement based on a color formation reaction, the mobile device having at least one camera, the method comprising:
a) evaluating the capability of the mobile device to have one or more relevant settings of the mobile device controlled by a user's software running on the mobile device, the relevant settings pertaining to image raw data processing steps to be carried out by the mobile device, wherein the relevant settings include at least one of: a color space transformation and a tone mapping transformation;
b) if the evaluation in step a) indicates that the mobile device is capable of having the one or more relevant settings controlled by the user's software, providing at least one item of control information, the at least one item of control information indicating that the mobile device is suitable for performing the analytical measurement; and
c) if the evaluation in step a) indicates that the mobile device is not capable of having the one or more relevant settings controlled by the user's software, providing at least one item of control information, the at least one item of control information indicating that the mobile device is unsuitable for performing the analytical measurement,
wherein in step a) the capability of the mobile device to have one or more relevant settings controlled is evaluated by trying to control the one or more relevant settings and then determining a success of the control, wherein the user's software is used to send a command for individual values of the one or more relevant settings to equal preset reference values and subsequently compare the one or more relevant settings with said one or more reference values.

* * * * *